US00PP36270P2

(12) United States Plant Patent
Mousa

(10) Patent No.: US PP36,270 P2
(45) Date of Patent: Nov. 26, 2024

(54) ***BEGONIA* PLANT NAMED 'Dobegmotwosal'**

(50) Latin Name: ***Begonia* x *hiemalis***
Varietal Denomination: Dobegmotwosal

(71) Applicant: DUMMEN GROUP B.V., De Lier (NL)

(72) Inventor: Rami Mousa, De Lier (NL)

(73) Assignee: DÜMMEN GROUP B.V., De Lier (NL)

( * ) Notice: Subject to any disclaimer, the term of this patent is extended or adjusted under 35 U.S.C. 154(b) by 0 days.

(21) Appl. No.: 18/543,903

(22) Filed: Dec. 18, 2023

(51) Int. Cl.
*A01H 5/02* (2018.01)
*A01H 6/18* (2018.01)

(52) U.S. Cl.
USPC ..... Plt./348

(58) Field of Classification Search
USPC ..... Plt./343, 344, 348
See application file for complete search history.

*Primary Examiner* — Susan McCormick Ewoldt
(74) *Attorney, Agent, or Firm* — C. Anne Whealy

(57) ABSTRACT

A new and distinct cultivar of *Begonia* plant named 'Dobegmotwosal', characterized by its relatively compact, upright and mounded plant habit; moderately vigorous growth habit; strong branching habit; dark green-colored leaves; freely and continuously flowering habit; and medium to large double-type flowers that are salmon pink in color.

1 Drawing Sheet

Botanical designation: *Begonia* x *hiemalis*.
Cultivar denomination: 'DOBEGMOTWOSAL'.

STATEMENT REGARDING PRIOR DISCLOSURES BY INVENTOR and APPLICANT/ASSIGNEE

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Begonia* plant, botanically known as *Begonia* x *hiemalis*, commercially referred to as an Elatior *Begonia* and hereinafter referred to by the name 'Dobegmotwosal'.

The new *Begonia* plant is a product of a planned breeding program conducted by the Inventor in De Lier, The Netherlands. The objective of the breeding program was to develop new freely flowering *Begonia* plants with strong branches and large double-type flowers.

The new *Begonia* plant is a naturally-occurring whole plant mutation of a proprietary selection of *Begonia* x *hiemalis* identified as code number BG15-000130-007, not patented. The new *Begonia* plant was discovered and selected by the Inventor as a single flowering plant from within a population of plants of the proprietary selection in a controlled greenhouse environment in De Lier, The Netherlands during the autumn of 2019.

Asexual reproduction of the new *Begonia* plant by vegetative tip cuttings in a controlled greenhouse environment in De Lier, The Netherlands since the autumn of 2019 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environment such as temperature and light intensity, without, however, any variance in genotype.

The following traits have been repeatedly observed and are determined to be the unique characteristics of 'Dobegmotwosal'. These characteristics in combination distinguish 'Dobegmotwosal' as a new and distinct *Begonia* plant:

1. Relatively compact, upright and mounded plant habit.
2. Moderately vigorous growth habit.
3. Strong branching habit.
4. Dark green-colored leaves.
5. Freely and continuously flowering habit.
6. Medium to large double-type flowers that are salmon pink in color.

Plants of the new *Begonia* can be compared to plants of the mutation parent selection. In side-by-side comparisons, plants of the new *Begonia* differ primarily from plants of the mutation parent selection in the following characteristics:

1. Plants of the new *Begonia* have larger and lighter green-colored leaves than plants of the mutation parent selection.
2. Flowers of plants of the new *Begonia* are salmon pink in color whereas flowers of plants of the mutation parent selection are orange in color.

Plants of the new *Begonia* can be compared to plants of *Begonia* x *hiemalis* 'Dobegmotwohopi', disclosed in a U.S. Plant patent application Ser. No. 18/543,880, filed concurrently. In side-by-side comparisons, plants of the new *Begonia* differ primarily from plants of 'Dobegmotwohopi' in the following characteristics:

1. Plants of the new *Begonia* have larger leaves than plants of 'Dobegmotwohopi'.
2. Flowers of plants of the new *Begonia* are salmon pink in color whereas flowers of plants of 'Dobegmotwohopi' are vivide purplish pink in color.

BRIEF DESCRIPTION OF THE PHOTOGRAPH

The accompanying colored photograph illustrates the overall appearance of the new *Begonia* plant showing the colors as true as it is reasonably possible to obtain in colored reproductions of this type. Colors in the photograph may differ slightly from the color values cited in the detailed botanical description which accurately describe the colors of the new *Begonia* plant.

The photograph is a side perspective view of a typical flowering plant of 'Dobegmotwosal' grown in a container.

DETAILED BOTANICAL DESCRIPTION

Plants used for the aforementioned photograph and following observations and measurements were grown in 12-cm containers during the summer in a glass-covered greenhouse in De Lier, The Netherlands. During the production of the plants, day temperatures ranged from 20 C to 35 C, night temperatures ranged from 17 C to 25 C and minimum light levels were 135 watt/$m^2$. Plants were twelve weeks old when the photograph and the description were taken. In the following description, color references are made to The Royal Horticultural Society Colour Chart, Fifth Edition, except where general terms of ordinary dictionary significance are used.

Botanical classification: *Begonia* x *hiemalis* 'Dobegmotwosal'.

Parentage: Naturally-occurring whole plant mutation of a proprietary selection of *Begonia* x *hiemalis* identified as code number BG15-000130-007, not patented.

Propagation:

*Type*.—By vegetative tip cuttings.

*Time to initiate roots, summer*.—About 15 days at temperatures about 22 C to 30 C.

*Time to initiate roots, winter*.—About 21 days at temperatures about 20 C to 22 C.

*Time to produce a rooted young plant, summer*.—About 22 to 25 days at temperatures about 22 C to 30 C.

*Time to produce a rooted young plant, winter*.—About 25 to 28 days at temperatures about 20 C to 22 C.

*Root description*.—Medium in thickness, fibrous; whitish grey in color, actual color of the roots is dependent on substrate composition, water quality, fertilizer type and formulation, substrate temperature and physiological age of roots; plants of the new *Begonia* have not been observed to form tubers.

*Rooting habit*.—Moderately freely branching; medium density.

Plant description:

*Plant form and growth habit*.—Relatively compact, upright to mounded plant habit; freely basal branching with about four primary lateral branches each with about four secondary lateral branches; moderately vigorous growth habit and moderate growth rate.

*Plant height, soil level to top of foliar plane*.—About 18 cm.

*Plant height, soil level to top of floral plane*.—About 20 cm.

*Plant width*.—About 30 cm.

*Lateral branch description*.—Length: About 13 cm. Diameter: About 1.4 cm. Internode length: About 2 cm. Texture and luster: Pubescent; semi-glossy. Aspect: Mostly upright. Strength: Moderately strong, flexible. Color, developing: Close to 146C. Color, developed: Close to 146C; at the internodes, close to 144B.

*Leaf description*.—Arrangement: Alternate, simple. Length: About 19 cm. Width: About 15 cm. Shape: Cordate. Apex: Narrowly acute. Base: Oblique. Margin: Serrate; sinuses medium in depth and divergent. Texture and luster, upper surface: Smooth, glabrous; semi-glossy. Texture and luster, lower surface: Pubescent; semi-glossy. Venation pattern: Palmate; reticulate. Color: Developing leaves, upper surface: Close to 147A. Developing leaves, lower surface: Close to 143A tinged with 51A. Fully expanded leaves, upper surface: Close to 147A; venation, close to 144B. Fully expanded leaves, lower surface: Close to 143A tinged with 59B; venation, close to 152D. Petioles: Length: About 4.5 cm. Diameter: About 7 mm. Texture and luster, upper and lower surfaces: Smooth, glabrous; semi-glossy. Strength: Moderately strong; flexible. Color, upper and lower surfaces: Close to 152B.

Flower description:

*Flowering habit*.—Fully double-type flowers arranged in axillary cymes; freely flowering habit with typically about two or three flowers per inflorescence and about 29 to 50 open flowers and flower buds per plant at one time; flowers face mostly upright to outwardly.

*Fragrance*.—None detected.

*Natural flowering season*.—Plants begin flowering about ten to twelve weeks after planting; long flowering period, in the garden plants flower freely and continuously from the late spring throughout the summer in Northern Europe and can be flowered year-round in greenhouses.

*Flower longevity*.—Depending on temperature, individual flowers last about four weeks on the plant; flowers persistent.

*Inflorescence height*.—About 6 cm.

*Inflorescence diameter*.—About 6 cm.

*Flower buds*.—Length: About 1.5 cm. Diameter: About 1.5 cm. Shape: Ovoid. Texture and luster: Smooth, glabrous; semi-glossy. Color: Close to 4C tinged with close to 29B.

*Flower size*.—Diameter: About 5.5 cm by 5.5 cm. Depth (height): About 2.5 cm.

*Petals*.—Quantity per flower and arrangement: Typically four to five per flower arranged in a single whorl. Length: About 2.8 cm. Width: About 3 cm. Shape: Obovate. Apex: Rounded and emarginate. Base: Cuneate and truncate. Margin: Entire; not undulate. Texture and luster, upper surface: Smooth, glabrous; matte. Texture and luster, lower surface: Smooth, glabrous; semi-glossy. Color: When opening and fully opened, upper surface: Close to 38A; color becoming closer to 38B with subsequent development. When opening and fully opened, lower surface: Close to 8B tinged with close to 38B; color becoming closer to 38B with subsequent development.

*Petaloids*.—Quantity per flower and arrangement: Typically 18 to 20 per flower arranged in about seven whorls. Length: About 2 cm. Width: About 1.7 cm. Shape: Obovate. Apex: Rounded. Base: Cuneate. Margin: Entire; slightly undulate. Texture and luster, upper and lower surfaces: Smooth, glabrous; semi-glossy. Color: When opening, upper and lower surfaces: Close to 37B. Fully opened, upper and lower surfaces: Close to 37B; venation, close to 38A; color does not change with subsequent development.

*Sepals*.—Quantity per flower and arrangement: Typically two per flower arranged in a single whorl. Length: About 1.2 cm. Width: About 9 mm. Shape: Obovate. Apex: Rounded and emarginate. Base: Cuneate and truncate. Margin: Entire. Texture and luster, upper and lower surfaces: Smooth, glabrous; semi-glossy. Color: When opening, upper surface: Close to 145B. When opening, lower surface: Close to 145A. Fully opened, upper and lower surfaces: Close to 145A.

*Peduncles*.—Length: About 4 cm. Diameter: About 4 mm. Aspect: Semi-upright. Strength: Moderately strong; flexible. Texture and luster: Smooth, glabrous; glossy. Color: Close to 144A tinged with close to 32A.

*Pedicels*.—Length: About 2 cm. Diameter: About 3 mm. Aspect: Upright to outwardly. Strength: Moderately strong; flexible. Texture and luster: Smooth, glabrous; glossy. Color: Close to 34B.

*Reproductive organs*.—All reproductive organs are transformed into tepaloids.

Pathogen & pest resistance: To date, resistance to pathogens and pests common to *Begonia* plants has not been observed on plants of the new *Begonia*.

Temperature tolerance: Plants of the new *Begonia* have been observed to tolerate temperatures ranging from about 10 C to about 35 C.

It is claimed:

1. A new and distinct *Begonia* plant named 'Dobegmotwosal' herein as illustrated and described.

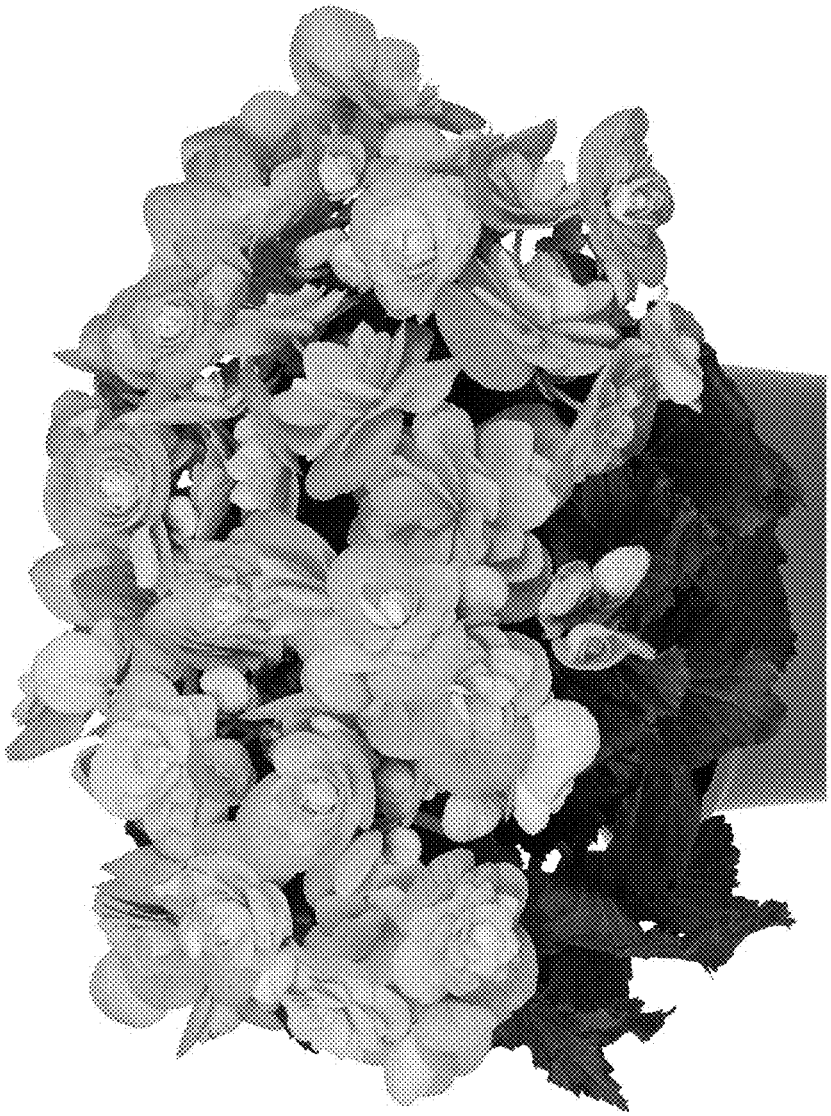

* * * * *